(12) United States Patent
Frey et al.

(10) Patent No.: US 9,284,253 B2
(45) Date of Patent: Mar. 15, 2016

(54) METHOD FOR PRODUCING POLYOL ESTERS

(71) Applicant: Oxea GmbH, Oberhausen (DE)

(72) Inventors: Guido D. Frey, Riedstadt (DE); Tonia Weber, Darmstadt (DE); Jörg Arnold, Dinslaken (DE); Thorsten Kreickmann, Oberhausen (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/427,742

(22) PCT Filed: Aug. 10, 2013

(86) PCT No.: PCT/EP2013/002408
§ 371 (c)(1),
(2) Date: Mar. 12, 2015

(87) PCT Pub. No.: WO2014/040680
PCT Pub. Date: Mar. 20, 2014

(65) Prior Publication Data
US 2015/0344400 A1    Dec. 3, 2015

(30) Foreign Application Priority Data
Sep. 14, 2012   (DE) .......................... 10 2012 018 207

(51) Int. Cl.
*C07C 67/08*    (2006.01)
(52) U.S. Cl.
CPC ..................................... *C07C 67/08* (2013.01)
(58) Field of Classification Search
CPC ..................................................... C07C 67/08
See application file for complete search history.

(56) References Cited

U.S. PATENT DOCUMENTS

| 4,304,925 A | 12/1981 | Watanabe et al. |
| 5,324,853 A | 6/1994 | Jones et al. |
| 8,399,697 B2 | 3/2013 | Weber et al. |
| 2011/0087044 A1* | 4/2011 | Weber .................... C07C 67/08 560/183 |
| 2012/0190883 A1 | 7/2012 | Frey et al. |

FOREIGN PATENT DOCUMENTS

| DE | 4002949 A1 | 8/1991 |
| DE | 102009048771 A1 | 4/2011 |
| DE | WO2012/019670 | * 2/2012 |
| EP | 0439722 A1 | 8/1991 |
| EP | 2308823 A2 | 4/2011 |
| WO | 2005021482 A1 | 3/2005 |
| WO | 2011042116 A1 | 4/2011 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*
White et al, Basic Energy Sciences Advisory Committee Subpanel Workshop Report, Opportunities for Catalysis in the 21st Century, 2002, pp. 1-47.*
Ishihara, Tetrahedron, Dehydrative Condensation Catalysts, 2009, 65, pp. 1085-1109.*
Mohammad-Khah et al, International Journal of ChemTech Research, Activated Charcoal: Preparation, characterization and Applications : A review article, 2009, 1(4), pp. 859-864.*
International Search Report dated Nov. 7, 2013.
International Preliminary Report on Patentability dated Apr. 9, 2015.

* cited by examiner

*Primary Examiner* — Paul A Zucker
(74) *Attorney, Agent, or Firm* — Michael W. Ferrell

(57) ABSTRACT

A process for preparing polyol esters by reacting polyols with linear or branched aliphatic monocarboxylic acids having 3 to 20 carbon atoms, is characterized in that a mixture of the starting compounds is allowed to react in the presence of a Lewis acid containing at least one element of groups 4 to 14 of the periodic table of the elements as a catalyst and in the presence of an adsorbent with removal of the water formed, and then the crude ester obtained is aftertreated by adding a further adsorbent which is an acidic activated carbon having a pH of 1 to 6.5.

15 Claims, No Drawings

US 9,284,253 B2

METHOD FOR PRODUCING POLYOL ESTERS

CLAIM FOR PRIORITY

This application is a national phase application of PCT/EP2013/002408 FILED Aug. 10, 2013 which was based on application DE 10 2012 018 207.4 FILED Sep. 14, 2012. The priorities of PCT/EP2013/002408 and DE 10 2012 018 207.4 are hereby claimed and their disclosures incorporated herein by reference.

TECHNICAL FIELD

The invention relates to a process for preparing polyol esters from linear or branched aliphatic monocarboxylic acids having 3 to 20 carbon atoms and polyols by converting the starting compounds in the presence of a Lewis acid containing at least one element of groups 4 to 14 of the periodic table of the elements as a catalyst and in the presence of an adsorbent and by subsequent aftertreatment of the crude ester by addition of a further adsorbent.

BACKGROUND

Esters of polyhydric alcohols, also called polyol esters, find a variety of uses on a large scale in industry, for example as plasticizers or lubricants. The selection of suitable starting materials allows the physical properties, for example boiling point or viscosity, to be controlled, and the chemical properties, such as hydrolysis resistance or stability to oxidative degradation, to be taken into account. Polyol esters can also be tailored to the solution of specific performance problems. Detailed overviews of the use of polyol esters can be found, for example, in Ullmann's Encyclopedia of Industrial Chemistry, 5th edition, 1985, VCH Verlagsgesellschaft, Vol. A1, pages 305-319; 1990, Vol. A15, pages 438-440, or in Kirk Othmer, Encyclopedia of Chemical Technology, 3rd edition, John Wiley & Sons, 1978, Vol. 1, pages 778-787; 1981, Vol. 14, pages 496-498.

The use of polyol esters as lubricants is of great industrial significance, and they are used particularly for those fields of use in which mineral oil-based lubricants meet the requirements set only incompletely. Polyol esters are used especially as turbine engine and instrument oils. Polyol esters for lubricant applications are based frequently on 1,3-propanediol, 1,3-butanediol, 1,4-butanediol, 1,2-hexanediol, 1,6-hexanediol, neopentyl glycol, trimethylolpropane, pentaerythritol, 2,2,4-trimethylpentane-1,3-diol, glycerol or 3(4),8(9)-dihydroxymethyltricyclo[5.2.1.0$^{2,6}$]decane, also known as TCD alcohol DM, as the alcohol component.

Polyol esters are also used to a considerable degree as plasticizers. Plasticizers find a variety of uses in plastics, coating materials, sealing materials and rubber articles. They interact physically with high-polymer thermoplastic substances, without reacting chemically, preferably by virtue of their swelling and dissolution capacity. This forms a homogeneous system, the thermoplastic range of which is shifted to lower temperatures compared to the original polymers, one result being that the mechanical properties thereof are optimized, for example deformation capacity, elasticity and strength are increased, and hardness is reduced.

In order to open up the widest possible fields of use to plasticizers, they must fulfil a series of criteria. They should ideally be odourless, colourless, and light-, cold- and heat-resistant. Moreover, it is expected that they are insensitive to water, comparatively nonflammable and not very volatile, and are not harmful to health. Furthermore, the production of the plasticizers should be simple and, in order to meet ecological requirements, avoid waste substances, such as by-products which cannot be utilized further and wastewaters comprising pollutants. A specific class of polyol esters (they are referred to as G esters for short) contains diols or ether diols as the alcohol component, for example ethylene glycol, diethylene glycol, triethylene glycol, tetraethylene glycol, 1,2-propylene glycol or higher propylene glycols. They can be prepared in different ways. In addition to the reaction of alcohol and acid, optionally in the presence of acidic catalysts, further processes are employed in practice to obtain G esters, including the reaction of diol with acid halide, the transesterification of a carboxylic ester with a diol, and the addition of ethylene oxide onto carboxylic acids (ethoxylation). In industrial manufacture, only the direct reaction of diol and carboxylic acid and the ethoxylation of carboxylic acids have become established as production processes, preference usually being given to the esterification of diol and acid. This is because this process can be performed with no particular complexity in conventional chemical apparatus, and it affords chemically homogeneous products. Compared to this, ethoxylation requires extensive and costly technical equipment.

The direct esterification of alcohols with carboxylic acids is one of the basic operations in organic chemistry. In order to increase the reaction rate, the conversion is typically performed in the presence of catalysts. The use of one of the reactants in excess and/or the removal of the water formed in the course of the reaction ensures that the equilibrium is shifted in accordance with the law of mass action to the side of the reaction product, i.e. of the ester, which means that high yields are achieved.

Comprehensive information regarding the preparation of esters of polyhydric alcohols, also including esters of ethylene glycols and fatty acids, and regarding the properties of selected representatives of these compound classes can be found in Goldsmith, Polyhydric Alcohol Esters of Fatty Acids, Chem. Rev. 33, 257 ff. (1943). For example, esters of diethylene glycol, of triethylene glycol and of polyethylene glycols are prepared at temperatures of 130 to 230° C. over reaction times of 2.5 to 8 hours. To remove the water of reaction, carbon dioxide is used. Suitable catalysts mentioned for the esterification of polyhydric alcohols are inorganic acids, acidic salts, organic sulphonic acids, acetyl chloride, metals or amphoteric metal oxides. The water of reaction is removed with the aid of an entraining agent, for example toluene or xylene, or by introducing inert gases such as carbon dioxide or nitrogen.

The production and the properties of fatty acid esters of the polyethylene glycols are discussed by Johnson (edit.), Fatty Acids in Industry (1989) Chapter 9, Polyoxyethylene Esters of Fatty Acids, and a series of preparative hints are given. Higher diester concentrations are achieved by the increase in the molar ratio of carboxylic acid to glycol. Suitable measures for removing the water of reaction are azeotropic distillation in the presence of a water-immiscible solvent, heating while passing through an inert gas, or performing the reaction under reduced pressure in the presence of a desiccant. When the addition of catalysts is dispensed with, longer reaction times and higher reaction temperatures are required. Both reaction conditions can be made milder by the use of catalysts. In addition to sulphuric acid, organic acids such as p-toluenesulphonic acid and cation exchangers of the polystyrene type are the preferred catalysts. The use of metal powders, such as tin or iron, is also described. According to the teaching from U.S. Pat. No. 2,628,249, colour problems in the case of catalysis with sulphuric acid or sulphonic acid can be alleviated when working in the presence of activated carbon.

As further metallic catalysts, titanium alkoxides, carboxylates or chelates, zirconium alkoxides, carboxylates or chelates or tin alkoxides, carboxylates or chelates are also used for preparation of polyol esters, for example according to U.S. Pat. No. 5,324,853 A1. Such metal catalysts can be regarded as high-temperature catalysts, since they do not reach their full activity until high esterification temperatures, generally above 180° C. They are frequently added not at the start of the esterification reaction but after the reaction mixture has already been heated up and has partly reacted with elimination of water. In spite of the higher reaction temperatures and longer reaction times required compared to conventional sulphuric acid catalysis, catalysis with such metal compounds affords crude esters having a comparatively low colour number. Commonly used esterification catalysts are, for example, tetraisopropyl orthotitanate, tetrabutyl orthotitanate, tetrabutyl zirconate or tin(II) 2-ethylhexanoate.

In the catalytic esterification reaction of polyols with carboxylic acids, based on the component present in deficiency, a high conversion is attained within a comparatively short time, but a comparatively long reaction time has to be accepted for the residual conversion to the desired polyol esters. In that case, a polyol ester having an acceptable residual content of partly esterified products is obtained, expressed by the hydroxyl number in mg KOH/g (according to DIN 53240) or by the content of partially esterified products determined by gas chromatography, but long reaction times are economically disadvantageous since they restrict the performance of the industrial production plant. In order also to accelerate the residual conversion, U.S. Pat. No. 5,324,853 A1 proposes vigorous mixing of the reaction mixture.

After the esterification reaction has ended, sufficient removal of the metal catalyst should be ensured, since metal traces in the purified polyol esters can impair the use thereof as plasticizers or lubricants, for example by influencing the electrical conductivity or the stability to atmospheric oxygen. According to the mode of operation from U.S. Pat. No. 5,324,853 A1, the crude esterification mixture is admixed with an aqueous soda solution and optionally with activated carbon. This mode of operation hydrolyses the metal compounds to insoluble solids, and they can be filtered off prior to the further workup of the crude ester compound. According to U.S. Pat. No. 4,304,925 A1, the crude esterification product, prior to addition of alkali, is first admixed with water and heat-treated. This converts the hydrolysed metal compounds to precipitates of good filterability.

According to WO 2011/042116 A1, the reaction of polyols with linear or branched aliphatic monocarboxylic acids having 3 to 20 carbon atoms is effected in the presence of a Lewis acid and in the presence of an adsorbent, followed by performance of a steam treatment. The steam treatment destroys catalyst residues still present and converts them to hydrolysis products of good filterability. The adsorbent already present during the esterification reaction facilitates the separation of the catalyst conversion products.

EP 2 308 823 A2 likewise relates to a process for preparing polyol esters by reacting polyols with linear or branched aliphatic monocarboxylic acids having 3 to 20 carbon atoms in the presence of an adsorbent. The polyol ester obtained can be subjected to another aftertreatment with an adsorbent.

EP 0 439 722 A1 concerns a process for workup of a crude ester mixture from the titanium-catalyzed reaction of primary C6 to C14 alcohols with di- and tricarboxylic acids or anhydrides thereof. After removing the unconverted alcohol, activated carbon is added and the residual alcohol is removed by treatment with steam.

WO 2005/021482 A1 also describes an esterification process in which the esterification reaction is followed by workup of the crude product by base treatment, steam treatment, filtration and another stripping operation. There follows a treatment with an adsorbent and subsequently the filtration of the adsorbent, optionally in the presence of a filtering aid. The adsorbent used is preferably activated carbon, which can also be used together with the filtering aid in the workup of the crude ester. Both the activated carbon and the filtering aid should each have a pH of 6 to 11.

The prior art regarding preparation of polyol esters under metal catalysis entails either a particular reactor design in order to complete the esterification reaction within an economically acceptable time or an additional treatment with water under hot conditions, for example also in the form of a steam treatment, in order to very substantially remove the metallic catalyst after the esterification reaction has ended to form hydrolysis products of good filterability.

The problem addressed was therefore that of improving the known processes and optimizing the process by balancing and simplifying the successive component steps in the overall process and simplifying the recovery of polyol esters in high quality, such that polyol esters can have maximum versatility of use.

SUMMARY OF INVENTION

The invention therefore consists in a process for preparing polyol esters by reacting polyols with linear or branched aliphatic monocarboxylic acids having 3 to 20 carbon atoms, characterized in that a mixture of the starting compounds is allowed to react in the presence of a Lewis acid containing at least one element of groups 4 to 14 of the periodic table of the elements as a catalyst and in the presence of an adsorbent with removal of the water formed, and then the crude ester obtained is aftertreated by adding a further adsorbent which is an acidic activated carbon having a pH of 1 to 6.5.

The reaction between the polyol and aliphatic monocarboxylic acid starting compounds, depending on the starting materials, sets in within the range from about 120 to 180° C., and can subsequently be conducted to completion in different ways.

In one configuration of the process according to the invention, the mixture is first heated proceeding from room temperature to a temperature up to a maximum of 280° C., preferably up to 250° C., and the pressure is lowered stage by stage proceeding from standard pressure with the temperature kept constant, in order to facilitate the removal of the water of reaction. The selection of the pressure stages, whether one, two or more than two stages, and of the pressure to be established at a particular stage, can be varied over a wide range and matched to the particular conditions. For example, in a first stage, the pressure can be lowered proceeding from standard pressure first down to 600 hPa, and then the reaction can be conducted to completion at a pressure of 300 hPa. These pressure figures are guide values which are appropriately complied with.

In addition to the variation of the pressure, it is likewise also possible to alter the temperature in one, two or more than two stages proceeding from room temperature during the esterification reaction, such that the temperature is increased from stage to stage at constant pressure, typically up to a maximum temperature of 280° C. However, it has been found to be appropriate to heat to a maximum of 280° C. with rising temperature from stage to stage, and also to lower the pressure from stage to stage. For example, the esterification reaction can be conducted proceeding from room temperature in a first stage at a temperature up to 190° C. A reduced pressure down to 600 hPa is likewise applied, in order to accelerate the driving-out of the water of reaction. After attainment of the temperature stage of 190° C., the pressure is lowered once again down to 300 hPa, and the esterification reaction is conducted to completion at a temperature up to 250° C. These temperature and pressure figures are guide values which are appropriately complied with. The temperature and pressure conditions to be established at the particular stages, the number of stages and the particular temperature increase or pressure reduction rate per unit time can be varied over a wide range and adjusted according to the physical properties of the starting compounds and of the reaction products, the temperature and pressure conditions of the first stage being established proceeding from standard pressure and room temperature. It has been found to be particularly appropriate to increase the temperature in two stages and to reduce the pressure in two stages.

The lower limit of the pressure to be established depends on the physical properties, such as boiling points and vapour pressures, of the starting compounds and of the reaction products formed, and is also determined by the plant equipment. Proceeding from standard pressure, it is possible to work stage by stage within these limits with pressures decreasing from stage to stage. The upper temperature limit, typically 280° C., should be complied with in order to avoid the formation of decomposition products, some of whose effects are detrimental in terms of colour. The lower limit of the temperature stages is determined by the reaction rate, which must still be sufficiently high to conclude the esterification reaction within an acceptable time. Within these limits, it is possible to work stage by stage with temperatures rising from stage to stage.

The particular reaction conditions, such as temperature, reaction time, pressure to be applied or catalyst to be used, should be tailored to the particular polyol ester, in order to force the formation of colouring components into the background and as far as possible to avoid degradation reactions of the polyol ester with a sufficient reaction rate. Especially in the case of polyol esters based on ether diols, for example triethylene glycol or tetraethylene glycol, enhanced degradation of the ether skeleton may set in when the reaction conditions, such as temperature, reaction time and type and amount of catalyst, are not adjusted in a controlled manner to the particular polyol ester.

The esterification can be undertaken with stoichiometric amounts of polyol and of aliphatic monocarboxylic acid. Preference is given, however, to allowing the polyol to react with excess monocarboxylic acid, which is generally the lower-boiling component and which can be removed by distillation in a simple manner in the subsequent workup of the crude ester. The aliphatic monocarboxylic acid is used in a 10 to 50% molar excess, preferably in a 20 to 40% molar excess, per mole of hydroxyl group to be esterified in the polyol.

The water of reaction formed is distilled out of the reaction vessel in the course of the esterification reaction together with the excess monocarboxylic acid and passed into a downstream phase separator in which monocarboxylic acid and water separate according to their solubility properties. Between the reaction vessel and phase separator, it is likewise possible to install a fractionating column having 1 to 25, preferably 2 to 10 and especially 3 to 6 theoretical plates, in which the water-enriched fraction is passed into the phase separator via the top of the column and the monocarboxylic acid-enriched fraction flows back into the reaction vessel via the bottom of the column.

In some cases, the monocarboxylic acid used also forms an azeotrope with water under the reaction conditions and is capable of removing the water of reaction as an entraining agent. The occurrence of water can be used to monitor the progress of the reaction. The water separated out is removed from the process, while the monocarboxylic acid flows out of the phase separator back into the reaction vessel. The addition of a further organic solvent, such as hexane, 1-hexene, cyclohexane, toluene, xylene or xylene isomer mixtures, which assumes the task of the azeotroping agent, is not ruled out, but is restricted to a few exceptional cases. The azeotroping agent can be added as early as at the start of the esterification reaction or after the attainment of relatively high temperatures. When the theoretically expected amount of water has been obtained or the hydroxyl number, for example determined to DIN 53240, has fallen below a set value, the reaction is ended by allowing the reaction mixture to cool.

DETAILED DESCRIPTION

The catalysts used for the esterification of the polyol with the monocarboxylic acid are Lewis acids containing at least one element of groups 4 to 14 of the Periodic Table of the Elements, which may be used in solid or liquid form. The term "Lewis acid" in the context of the invention is understood to mean the generally customary definition of those elements or compounds which have an electron vacancy, as explained, for example, in Römpp's Chemie-Lexikon, $8^{th}$ edition, Franck'sche Verlagshandlung 1983, Volume 3, H-L. The particularly suitable Lewis acids which can be used as catalysts in the esterification reaction include titanium, zirconium, hafnium, iron, zinc, boron, aluminium or tin, which are used in the form of the element in finely distributed form or preferably in the form of compounds. Suitable compounds are, for example, tin(II) oxide, tin(IV) oxide, tin carboxylates such as tin(II) 2-ethylhexanoate, tin(II) oxalate, tin(II) acetate or tin(IV) acetate, tin(IV) alkoxides such as tetramethyl stannate, tetraethyl stannate, tetrapropyl stannate, tetraisopropyl stannate or tetraisobutyl stannate, or organotin compounds such as butyltin maleate or dibutyltin dilaurate.

The suitable titanium compounds include alkoxides such as tetramethyl orthotitanate, tetraethyl orthotitanate, tetrapropyl orthotitanate, tetraisopropyl orthotitanate, tetrabutyl orthotitanate, tetraisobutyl orthotitanate, tetrapentyl orthotitanate or tetra(2-ethylhexyl) orthotitanate; acylates such as hydroxytitanium acetate, hydroxytitanium butyrate or hydroxytitanium pentanoate; carboxylates such as titanium (IV) acetate, titanium(IV) propionate, titanium(IV) butyrate, titanium(IV) pentanoate or titanium(IV) 2-ethylhexanoate; or chelates such as tetraethylene glycol titanate or tetrapropylene glycol titanate. It is also possible to successfully use the corresponding zirconium or hafnium compounds, such as tetramethyl orthozirconate, tetraethyl orthozirconate, tetrapropyl orthozirconate, tetraisopropyl orthozirconate, tetrabutyl orthozirconate, tetraisobutyl orthozirconate, tetrapentyl orthozirconate or tetra(2-ethylhexyl) orthozirconate.

Likewise suitable are boric acid and boric esters, such as trimethyl borate, triethyl borate, tripropyl borate, triisopropyl borate, tributyl borate or triisobutyl borate.

Likewise suitable are aluminium oxide, aluminium hydroxide, aluminium carboxylates such as aluminium acetate or aluminium stearate, or aluminium alkoxides such as aluminium tributoxide, aluminium tri-sec-butoxide, aluminium tri-tert-butoxide or aluminium triisopropoxide.

It is also possible to use zinc oxide, zinc sulphate and zinc carboxylates such as zinc acetate dihydrate or zinc stearate, and iron(II) acetate or iron(III) hydroxide oxide as catalysts.

The catalyst can be added to the reaction mixture as early as at the start, or only subsequently with observation of safety measures at elevated temperature, when, for example, the removal of the water of reaction has set in. The catalyst can be added in one portion or in a plurality of portions. It is particularly advisable to add a residual amount of catalyst towards the end of the esterification reaction.

The amount of the esterification catalyst added is $1 \times 10^{-5}$ to 20 mol %, preferably 0.01 to 5 mol %, especially 0.01 to 2 mol %, based on the starting compound added in deficiency, appropriately based on polyol. In the case of higher amounts of catalyst, cleavage reactions of the polyol esters are to be expected.

Particularly in the case of the preparation of polyol esters based on ether diols, for example triethylene glycol or tetraethylene glycol, in the case of use of high catalyst concentrations toward the end of the reaction and in the phase of the conversion of last residues of free hydroxyl groups, there is a risk of enhanced cleavage of the ether chain, such that the reaction temperature or the pressure to be applied should be adjusted in this case. The higher the catalyst concentration selected is, the lower the reaction temperature or the pressure to be applied should generally be selected, and an optimized temperature and pressure profile should be employed. In the case of excessively low catalyst concentrations, the esterification rate becomes so low that an acceptable conversion is not observed within an acceptable reaction time.

The esterification catalyst can be added in liquid or solid form. Solid catalysts, for example tin(II) oxide, zinc oxide or iron(III) hydroxide oxide are removed after the esterification reaction has ended, in the course of further workup. When the esterification catalysts are added in the form of liquid compounds, for example tetra(isopropyl) orthotitanate or tetra(butyl) orthotitanate, which are still present dissolved in the reaction mixture after the esterification reaction has ended, these compounds are converted in the course of the workup process to conversion products which can be removed by means of the adsorbent present in the esterification reaction and by means of the acidic activated carbon added during the aftertreatment.

The esterification is performed in the presence of an adsorbent. In this case, porous, solid materials of high surface area are used, which are typically used in chemical practice both in the laboratory and in industrial plants. Examples of such materials are polysilicic acids of high surface area, such as silica gels (silica xerogels), kieselguhr, high-surface area aluminium oxides and aluminium oxide hydrates, mineral materials such as clays or carbonates, or activated carbon. Activated carbon has been found to be particularly useful. In general, the adsorbent is suspended in finely divided form in the reaction solution, which is agitated by intensive stirring or by introducing an inert gas. This achieves intimate contact between the liquid phase and the adsorbent. The amount of the adsorbent can be adjusted substantially freely and hence according to the individual requirements. Based on 100 parts by weight of the liquid reaction mixture, it has proved useful to use 0.1 to 5 and preferably 0.5 to 1.5 parts by weight of the adsorbent.

Owing to the quality criteria described at the outset for polyol esters, the process steps in the esterification stage with removal of the water of reaction and in the workup of the crude ester are very important process features, since the adjustment of these process steps influences the sensory and optical properties of the end products, and also the residual content of catalyst, to a significant degree. More particularly, an optimized process regime affords polyol esters based on ether diols, for example triethylene glycol or tetraethylene glycol, with high purity, and also low colour number and high colour stability. The structure of the starting materials, of the polyhydric alcohols and of the aliphatic monocarboxylic acids is, in contrast, crucial for the mechanical and thermal properties of the polymer materials plasticized with the polyol esters, and influences the hydrolysis and oxidation stability of lubricants.

The reaction mixture obtained after the reaction has ended comprises, as well as the polyol ester as the desired reaction product, any unconverted starting materials, more particularly aliphatic monocarboxylic acid still in excess, when the preferred configuration of the process according to the invention with a monocarboxylic acid excess is employed. Typically, unconverted starting compounds present in excess are first distilled off, appropriately with application of a reduced pressure.

Subsequently, an acidic activated carbon is added to the crude ester, and this, for example, is suspended in finely divided form in the crude ester to be treated, for example by vigorous stirring or introduction of an inert gas. Based on 100 parts by weight of crude ester to be treated, generally 0.05 to 2.5 and preferably 0.1 to 0.75 parts by weight of the acidic activated carbon are added. In general, the amount of the acidic activated carbon added to the crude ester is much smaller compared to the amount of adsorbent present during the esterification reaction, and it is typically up to 50% of the amount added during the esterification reaction. The crude ester is treated with the acidic activated carbon generally at temperatures of room temperature to 140° C., preferably of 60 to 120° C., and generally over a period of 0.5 to 4 hours, preferably of 0.5 to 2 hours.

In a further configuration of the process according to the invention, the acidic activated carbon is added after the esterification reaction has ended but before removal or during the removal of the starting compound present in excess, typically the monocarboxylic acid. In this variant, the acidic activated carbon is already present in the course of removal of the majority of the excess starting compound. In this case, the aftertreatment of the crude ester with the acidic activated carbon is effected under the conditions which exist in the course of removal of the starting compounds present in excess.

It has been found that, surprisingly, the aftertreatment with the acidic activated carbon can distinctly reduce the residual content of the Lewis acid catalyst in the crude product. The more acidic the activated carbon or the lower the pH of the activated carbon, the greater the reduction in the residual content of the Lewis acid catalyst. The pH of the activated carbon in the context of the present invention is based on the pH of an aqueous extract which is obtained by suspending 5 grams of the acidic activated carbon in 100 ml of deionized water at 95° C. over one hour. Subsequently, the pH is measured at 25° C. If a strongly acidic activated carbon for which the aqueous extract has a pH less than 5.5 is used as the acidic activated carbon, the content of the Lewis acid catalyst in the crude product can be reduced to such an extent that the steam treatment proposed in WO 2011/042116 A1 can be dispensed with. Since the esterification plant is occupied by the time-consuming steam treatment, dispensing with this measure can improve plant deployment and the economic viability of the esterification process. This result was not to be expected since the adsorption of the acidic Lewis acid catalyst and of the degradation products thereof should if anything proceed on an alkaline adsorbent.

If an acidic activated carbon is used which is less acidic and whose aqueous extract has a pH of 5.5 to 6.5, a steam treatment in the presence of the acidic activated carbon is advisable, but this is distinctly shortened compared to a steam treatment in which a basic adsorbent is present. While the prior art according to WO 2011/042116 A1 teaches a duration for the steam treatment of 30 minutes to 5 hours, the duration of the optional steam treatment in the presence of moderately acidic activated carbon can be reduced to a period down to 30 minutes. Even shortening of the steam treatment from typically 90 to 120 minutes to 45 minutes increases the economic viability of the esterification process. Nevertheless, even in the case of use of moderately acidic activated carbon, a steam treatment is not absolutely necessary to suppress the residual content of Lewis acid catalyst to an acceptable level.

If the further adsorbents used are those adsorbents whose aqueous extract exhibits a pH of greater than 6.5, a steam treatment in the presence of the further adsorbent is very advisable, this generally being performed over a period of 30 minutes to 2 hours. In general, it can be stated that the more basic the further adsorbent added in the aftertreatment and the higher the pH of the aqueous extract, the longer the optional steam treatment which should be performed.

The acidic activated carbon which is added for the aftertreatment of the crude ester is porous solid activated carbon of high surface area, which is activated, for example. The activation of the activated carbons can be effected, for example, by means of steam, and this influences the acidic character of the activated carbon. Acidic activated carbons having a pH of 1 to 6.5, preferably of 2 to 5.5, are used, such as the commercially available types CA1 or SX 1G from Norit, or DCL 330 from Chemviron Carbon. It is likewise possible to use mixtures of different acidic activated carbons.

The optional steam treatment is generally performed at standard pressure, although the employment of a slightly reduced pressure, appropriately down to 400 hPa, is not ruled out. The steam treatment is effected generally at temperatures of 100 to 250° C., preferably of 150 to 220° C. and especially of 170 to 200° C., and is also guided by the physical properties of the polyol esters to be prepared in each case.

In the process step of optional steam treatment, it is found to be appropriate to proceed in a very gentle manner during the heating period until the attainment of the working temperature in order to heat the crude ester to the required temperature for the steam treatment.

The gentle steam treatment can suppress degradation reactions, especially the unwanted degradation of the ether chain in the course of preparation of polyol esters based on ether diols, for example triethylene glycol or tetraethylene glycol.

Optionally, the steam treatment is followed by the addition of a solid alkaline substance, for example basic silica, basic alumina or sodium carbonate, sodium hydrogencarbonate, calcium carbonate or sodium hydroxide in solid form, and basic minerals, in order to further reduce the neutralization number of the polyol ester.

Subsequently, the crude product is filtered, typically at temperatures of 40 to 120° C., and removed from the acidic activated carbon added during the aftertreatment and the adsorbent added during the esterification, from the catalyst degradation products and any solid alkaline substances added. The filtration can be supported by standard filtering aids such as cellulose, silica gel, kieselguhr or sawdust.

This is followed by the drying of the polyol ester, for example by passing an inert gas through the product at elevated temperature. It is also possible to simultaneously apply a reduced pressure at elevated temperature and optionally to pass an inert gas through the product. Even without involvement of an inert gas, it is possible to work only at elevated temperature or only at relatively low pressure. The particular drying conditions, such as temperature, pressure and duration, can be determined by simple preliminary tests. In general, temperatures in the range from 80 to 250° C. and preferably 100 to 180° C. and pressures of 0.2 to 500 hPa, preferably 1 to 200 hPa and especially 1 to 20 hPa are employed. The drying removes residues of starting compounds, for example monocarboxylic acid, and water. Thereafter, the dried polyol ester is freed of the last solids by filtration. The filtration is effected in conventional filtration apparatuses at standard temperature or at temperatures up to 120° C., optionally in the presence of standard filtering aids.

After completion of the filtration, light-coloured polyol esters are obtained, and these also meet the remaining specifications, such as water content, residual acid content, residual content of catalyst constituents and residual content of monoester.

The polyhydric alcohols or polyols used as starting materials for the process according to the invention satisfy the general formula (I)

$$R(OH)_n \qquad (I)$$

in which R is an aliphatic or cycloaliphatic hydrocarbon radical having 2 to 20 and preferably 2 to 10 carbon atoms, and n is an integer from 2 to 8, preferably 2, 3, 4, 5 or 6.

Suitable polyols are likewise compounds of the general formula (II)

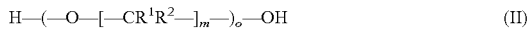

$$H-(-O-[-CR^1R^2-]_m-)_o-OH \qquad (II)$$

in which $R^1$ and $R^2$ are each independently hydrogen, an alkyl radical having 1 to 5 carbon atoms, preferably methyl, ethyl or propyl, or a hydroxyalkyl radical having 1 to 5 carbon atoms, preferably the hydroxymethyl radical, m is an integer from 1 to 10, preferably 1 to 8 and especially 1, 2, 3 or 4, o is an integer from 2 to 15, preferably 2 to 8 and especially 2, 3, 4 or 5.

Suitable polyols which can be converted by the process according to the invention to light-coloured polyol esters are, for example, 1,3-propanediol, 1,3-butanediol, 1,4-butanediol, neopentyl glycol, 2,2-dimethylolbutane, trimethylolethane, trimethylolpropane, ditrimethylolpropane, trimethylolbutane, 2,2,4-trimethylpentane-1,3-diol, 1,2-hexanediol, 1,6-hexanediol, pentaerythritol or dipentaerythritol or 3(4),8(9)-dihydroxymethyltricyclo[5.2.1.0$^{2,6}$]decane.

Useful further polyols include ethylene glycol and 1,2-propylene glycol, and the oligomers thereof, especially the ether diols di-, tri- and tetraethylene glycol or dipropylene glycol, tripropylene glycol or tetrapropylene glycol. Ethylene and propylene glycols are industrially produced chemicals. The base substance for preparation thereof is ethylene oxide and propylene oxide, from which 1,2-ethylene glycol and 1,2-propylene glycol are obtained by heating with water under pressure. Diethylene glycol is obtained by ethoxylation from ethylene glycol. Triethylene glycol is obtained, like tetraethylene glycol, as a by-product in the hydrolysis of ethylene oxide to prepare ethylene glycol. Both compounds can also be synthesized by reacting ethylene glycol with ethylene oxide. Dipropylene glycol, tripropylene glycol, tetrapropylene glycol and higher propoxylation products are obtainable from the multiple addition of propylene oxide onto 1,2-propylene glycol.

To obtain light-coloured polyol esters by the process according to the invention, linear or branched, aliphatic monocarboxylic acids having 3 to 20 carbon atoms in the molecule are used. Even though preference is given to saturated acids in many cases, depending on the particular field of use of the plasticizers or lubricants, it is also possible to use unsaturated carboxylic acids as a reaction component for ester synthesis. Examples of monocarboxylic acids as components of polyol esters are propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, cyclohexanecarboxylic acid, 2-ethylhexanoic acid, n-nonanoic acid, 2-methyloctanoic acid, isononanoic acid, 3,5,5-trimethylhexanoic acid, 2-propylheptanoic acid, 2-methylundecanoic acid, isoundecanecarboxylic acid, tricyclodecanecarboxylic acid and isotridecanecarboxylic acid. The novel process has been found to be particularly useful for the preparation of polyol esters of monoethylene glycol, or of the oligomeric ethylene glycols and of 1,2-propylene glycol, or of the oligomeric propylene glycols with $C_4$- to $C_{13}$- or $C_5$- to $C_{10}$-monocarboxylic acids, and for preparation of polyol esters based on 1,3-butanediol, neopentyl glycol, 2,2,4-trimethylpentane-1,3-diol, trimethylolpropane, ditrimethylolpropane, pentaerythritol or 3(4),8(9)-dihydroxymethyltricyclo[5.2.1.0$^{2,6}$]decane.

The polyol esters of ethylene glycol and the oligomers thereof are outstandingly suitable as plasticizers for all common high-polymer thermoplastic substances. They have been found to be particularly useful as an additive to polyvinyl butyral which is used admixed with glycol esters as an intermediate layer for production of multilayer or composite glasses. They can likewise be used as coalescence agents or film-forming assistants in aqueous dispersions of polymers which find various uses as coating materials. The preparation process according to the invention makes it possible to prepare, in a simple manner, polyol esters with outstanding colour properties which also satisfy further quality demands, such as low odour, a low acid number and a low level of catalyst impurities. The process according to the invention is particularly suitable for preparing triethylene glycol di-2-ethylhexanoate (3G8 Ester), tetraethylene glycol di-n-heptanoate (4G7 Ester), triethylene glycol di-2-ethylbutyrate (3G6 Ester), triethylene glycol di-n-heptanoate (3G7 Ester) or tetraethylene glycol di-2-ethylhexanoate (4G8 Ester).

The process according to the invention can be performed continuously or batchwise in the reaction apparatus typical for chemical technology. Useful apparatus has been found to be stirred tanks, including cascaded tank systems, or reaction tubes, the batchwise reaction regime being preferred.

The process according to the invention is illustrated in detail in the examples which follow.

WORKING EXAMPLES

For the determination of the pH of the activated carbons and adsorbents used in the aftertreatment, an aqueous extract was first produced by stirring 5 grams of the activated carbon used or of the adsorbent with 100 ml of deionized water at 95° C. over 1 hour to give a suspension. Subsequently, the pH was measured at 25° C. on the aqueous extract of the suspension. The measurements were conducted with the Schott CG836 pH meter.

Examples 1-5

Preparation of triethylene glycol di-2-ethylhexanoate (3G8 Ester)

A heatable 2 l four-neck flask provided with stirrer, internal thermometer and water separator was initially charged with triethylene glycol and 2-ethylhexanoic acid in a 30 mol % excess, based on the hydroxyl group to be esterified, and 0.045 mol % of tetraisopropyl orthotitanate, based on triethylene glycol, and 1% by weight of activated carbon of the Nuchar RGC type from Mead Westvaco, based on the overall reaction mixture, was added. While stirring and with application of a reduced pressure down to 600 hPa, the mixture was heated to 220° C. and water of reaction formed was removed on the water separator. After a reaction time of 1 hour at this level, the pressure was lowered to 400 hPa and the temperature was left at 220° C. After a further 3 hours of reaction time, the pressure was reduced further to 300 hPa. The course of the reaction was monitored by continuous weighing of the water of reaction discharged via the water separator, and by sampling and gas chromatography analysis of the samples. In the event of a content determined by gas chromatography (% by weight) of triethylene glycol di-2-ethylhexanoate of at least 97% and in the event of a residual hydroxyl number of not more than 5.0 mg KOH/g (DIN 53240), the reaction was ended. The pure esterification time beginning with the first occurrence of water was 8 hours. This was followed by distillative removal of the excess 2-ethylhexanoic acid at 180° C. and 2 hPa down to a residual acid content in the crude ester of 0.18 mg KOH/g (DIN EN ISO 2114/ASTM D 1613) and a Hazen colour number (DIN EN ISO 6271) of 239.

After the residual acid removal had ended, the titanium content in the crude ester was determined to be 18 ppm of titanium. According to Table 1, activated carbon was additionally added in an amount of 0.36% by weight, based on the total mass of the crude ester, and aftertreatment was effected at 90° C. while stirring. The titanium content in the crude ester was determined over the treatment time to ASTM D 5185.

TABLE 1

Aftertreatment with various activated carbon types at 90° C.

| | Example | | | | |
|---|---|---|---|---|---|
| | 1 | 2 | 3 | 4 | 5 |
| Activated carbon used | Norit CA1 | Chemviron Carbon DCL 330 | Norit SX 1G | Nuchar RGC (Comparison) | Norit SA Plus (Comparison) |
| pH of the activated carbon | 2.0-2.1 | 4.1-5.1 | 6.2-6.5 | 7.5-8.8 | 9.5-10.5 |
| Starting Ti content [ppm] | 18.0 | 18.0 | 18.0 | 18.0 | 18.0 |
| Ti content [ppm] after 20 min. | 0.7 | 1.0 | 9.6 | 10.5 | 13.3 |
| Ti content [ppm] after 40 min. | <0.5 | 0.6 | 8.2 | 9.9 | 12.7 |
| Ti content [ppm] after 60 min. | <0.5 | 0.5 | 7.4 | 9.5 | 12.5 |
| Ti content [ppm] after 120 min. | <0.5 | <0.5 | 6.1 | 9.0 | 11.6 |
| Hazen colour number after 120 min. | 108 | 175 | 159 | 116 | 178 |
| Acid number after 120 min. [mg KOH/g] | 0.22 | 0.18 | 0.17 | 0.16 | 0.12 |

TABLE 1-continued

Aftertreatment with various activated carbon types at 90° C.

| | Example | | | | |
|---|---|---|---|---|---|
| | 1 | 2 | 3 | 4 | 5 |
| Fe, Cr, Ni, Mn, Al, Sn content after 120 min. [ppm] | <1 | <1 | <1 | <1 | <1 |
| K content after 120 min. [ppm] | <5 | <1 | <5 | <5 | <5 |

Examples 6-8

Preparation of triethylene glycol di-2-ethylhexanoate (3G8 Ester)

A heatable 2 l four-neck flask provided with stirrer, internal thermometer and water separator was initially charged with triethylene glycol and 2-ethylhexanoic acid in a 30 mol % excess, based on the hydroxyl group to be esterified, and 0.045 mol % of tetraisopropyl orthotitanate, based on triethylene glycol, and 1% by weight of activated carbon of the Nuchar RGC type from Mead Westvaco, based on the overall reaction mixture, was added. While stirring and with application of a reduced pressure down to 600 hPa, the mixture was heated to 220° C. and water of reaction formed was removed on the water separator. After a reaction time of 1 hour at this level, the pressure was lowered to 400 hPa and the temperature was left at 220° C. After a further 3 hours of reaction time, the pressure was reduced further to 300 hPa. The course of the reaction was monitored by continuous weighing of the water of reaction discharged via the water separator, and by sampling and gas chromatography analysis of the samples. In the event of a content determined by gas chromatography (% by weight) of triethylene glycol di-2-ethylhexanoate of at least 97% and in the event of a residual hydroxyl number of not more than 5.0 mg KOH/g (DIN 53240), the reaction was ended. The pure esterification time beginning with the first occurrence of water was 8 hours. This was followed by distillative removal of the excess 2-ethylhexanoic acid at 180° C. and 2 hPa down to a residual acid content in the crude ester of 0.12 mg KOH/g (DIN EN ISO 2114/ASTM D 1613) and a Hazen colour number (DIN EN ISO 6271) of 135.

After the residual acid removal had ended, the titanium content in the crude ester was determined to be titanium content 14.6 ppm. According to Table 2, activated carbon was additionally added in an amount of 0.36% by weight, based on the total mass of the crude ester, and aftertreatment was effected at 65° C. while stirring. The titanium content in the crude ester was determined over the treatment time to ASTM D 5185.

TABLE 2

Aftertreatment with various activated carbon types at 65° C.

| | Example | | |
|---|---|---|---|
| | 6 | 7 | 8 |
| Activated carbon used | Chemviron Carbon DCL 330 | Norit D Ultra (Comparison) | Norit SA 4 PAH (Comparison) |
| pH of the activated carbon | 4.1-5.1 | 9.0-9.6 | 10.5-11.1 |
| Starting Ti content [ppm] | 14.6 | 14.6 | 14.6 |
| Ti content [ppm] after 20 min. | 2.4 | 13.1 | 12.9 |
| Ti content [ppm] after 40 min. | 1.5 | 13.0 | 12.7 |
| Ti content [ppm] after 60 min. | 1.1 | 12.3 | 12.5 |
| Ti content [ppm] after 120 min. | 0.6 | 11.6 | 11.7 |
| Hazen colour number after 120 min. | 135 | 200 | 198 |
| Fe, Cr, Ni, Mn, Al, Sn, K content after 120 min. [ppm] | <1 | <1 | <1 |
| K content after 120 min. [ppm] | <1 | <1 | <1 |

Examples 9-11

Preparation of triethylene glycol di-2-ethylhexanoate (3G8 Ester)

A heatable 2 l four-neck flask provided with stirrer, internal thermometer and water separator was initially charged with triethylene glycol and 2-ethylhexanoic acid in a 30 mol % excess, based on the hydroxyl group to be esterified, and 0.045 mol % of tetraisopropyl orthotitanate, based on triethylene glycol, and 1% by weight of activated carbon of the Nuchar RGC type from Mead Westvaco, based on the overall reaction mixture, was added. While stirring and with application of a reduced pressure down to 600 hPa, the mixture was heated to 220° C. and water of reaction formed was removed on the water separator. After a reaction time of 1 hour at this level, the pressure was lowered to 400 hPa and the temperature was left at 220° C. After a further 3 hours of reaction time, the pressure was reduced further to 300 hPa. The course of the reaction was monitored by continuous weighing of the water of reaction discharged via the water separator, and by sampling and gas chromatography analysis of the samples. In the event of a content determined by gas chromatography (% by weight) of triethylene glycol di-2-ethylhexanoate of at least 97% and in the event of a residual hydroxyl number of not more than 5.0 mg KOH/g (DIN 53240), the reaction was ended. The pure esterification time beginning with the first occurrence of water was 8 hours. This was followed by distillative removal of the excess 2-ethylhexanoic acid at 180° C. and 2 hPa down to a residual acid content in the crude ester of 0.38 mg KOH/g (DIN EN ISO 2114/ASTM D 1613).

After the residual acid removal had ended, the titanium content in the crude ester was determined to be titanium content 35 ppm. According to Table 3, an adsorbent was additionally added in an amount of 0.36% by weight, based on the total mass of the crude ester, (experiments 9 and 10) and aftertreatment was effected at 90° C. while stirring. The titanium content in the crude ester was determined over the treatment time to ASTM D 5185.

The workup of the crude ester having a titanium content of 35 ppm in experiment 11 was effected by addition of 0.18% by weight of activated carbon of the DCL 330 type from Chemviron Carbon, based on the total mass of the crude ester, with a steam treatment at 180° C. while stirring for 30 minutes.

TABLE 3

Aftertreatment with various adsorbents; activated carbon with steam treatment

| | Example | | |
|---|---|---|---|
| | 9 | 10 | 11 |
| Adsorbent/activated carbon used | Tonsil from Süd-Chemie (Comparison) | Aluminium oxide 90 active acidic; from Merck (Comparison) | Chemviron Carbon DCL 330; with steam treatment |
| pH of the adsorbent/activated carbon | 8.2 | 4.1 | 4.1-5.1 |
| Starting Ti content [ppm] | 35 | 35 | 35 |
| Ti content [ppm] after 20 min. | 13 | 30 | — |
| Ti content [ppm] after 30 min. | — | — | <0.5 |
| Ti content [ppm] after 40 min. | 10 | 29 | — |
| Ti content [ppm] after 60 min. | 9.6 | 27 | — |
| Ti content [ppm] after 120 min. | 8.1 | 26 | — |
| Hazen colour number after 120 min. | 237 | 334 | 159 |
| Fe, Cr, Ni, Mn, Al, Sn, K content after 120 min. [ppm] | <1 | <1 | <1 |
| K content after 120 min. [ppm] | <5 | <5 | <5 |

As the working examples show, the aftertreatment with an acidic activated carbon can distinctly reduce the content of the Lewis acid catalyst in the crude ester. The more acidic the activated carbon, the more marked this effect is. The combination of an aftertreatment with a moderately acidic activated carbon with a short steam treatment also distinctly lowers the content of the Lewis acid catalyst.

The invention claimed is:

1. Process for preparing polyol esters by reacting polyols of the general formula (II)

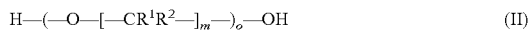

(II)

in which $R^1$ and $R^2$ are each independently hydrogen, an alkyl radical having 1 to 5 carbon atoms or a hydroxyalkyl radical having 1 to 5 carbon atoms, m is an integer from 1 to 10, and o is an integer from 2 to 15 with linear or branched aliphatic monocarboxylic acids having 3 to 20 carbon atoms, characterized in that a mixture of the starting compounds is allowed to react in the presence of a catalyst selected from the group consisting of titanium, zirconium, hafnium or tin as elements or in the form of compounds thereof and in the presence of an activated carbon adsorbent with removal of the water formed, and then the crude ester obtained is aftertreated by adding a further adsorbent which is an acidic activated carbon having a pH of 1 to 6.5.

2. Process according to claim 1, characterized in that the aftertreatment with the acidic activated carbon is effected at a temperature of room temperature to 140° C.

3. Process according to claim 1, characterized in that a steam treatment is performed in the presence of the acidic activated carbon.

4. Process according to claim 3, characterized in that the steam treatment is performed at a temperature of 100 to 250° C.

5. Process according to claim 1, characterized in that the polyol ester is dried at temperatures of 80 to 250° C. and at pressures of 0.2 to 500 hPa.

6. Process according to claim 1, characterized in that the acidic activated carbon has a pH of 2 to 5.5.

7. Process according to claim 1, characterized in that 0.05 to 2.5 parts by weight of the acidic activated carbon are added per 100 parts by weight of crude ester to be treated.

8. Process according to claim 1, characterized in that the catalyst is used in an amount of $1.0 \times 10^{-5}$ to 20 mol %, based on the starting compound used in deficiency.

9. Process according to claim 8, characterized in that the catalyst is used in an amount of 0.01 to 5 mol %, based on the starting compound used in deficiency.

10. Process according to claim 1, characterized in that the tin compounds used are tin(II) oxide, tin(II) oxalate, tin(II) carboxylates, tin(IV) alkoxides or organotin compounds.

11. Process according to claim 1, characterized in that the titanium compounds used are alkoxides, acylates, carboxylates or chelates.

12. Process according to claim 1, characterized in that 0.1 to 5 parts by weight of activated carbon are used in the reaction of polyols with linear or branched aliphatic monocarboxylic acids having 3 to 20 carbon atoms per 100 parts by weight of reaction mixture.

13. Process according to claim 1, characterized in that the polyols used are ditrimethylolpropane, dipentaerythritol, diethylene glycol, triethylene glycol, tetraethylene glycol, dipropylene glycol, tripropylene glycol or tetrapropylene glycol.

14. Process according to claim 1, characterized in that the aliphatic monocarboxylic acid converted is propionic acid, n-butyric acid, isobutyric acid, n-pentanoic acid, 2-methylbutyric acid, 3-methylbutyric acid, 2-methylpentanoic acid, n-hexanoic acid, 2-ethylbutyric acid, n-heptanoic acid, 2-methylhexanoic acid, 2-ethylhexanoic acid, n-nonanoic acid, 2-methyloctanoic acid, isononanoic acid, 3,5,5-trimethylhexanoic acid or 2-propylheptanoic acid.

15. Process according to claim 1 for preparation of triethylene glycol di-2-ethylhexanoate, tetraethylene glycol di-n-heptanoate, triethylene glycol di-2-ethylbutyrate, triethylene glycol di-n-heptanoate or tetraethylene glycol di-2-ethylhexanoate.

* * * * *